United States Patent
Krueger et al.

(10) Patent No.: US 12,419,667 B2
(45) Date of Patent: Sep. 23, 2025

(54) SURGICAL FIXATION SYSTEM

(71) Applicant: Aesculap AG, Tuttlingen (DE)

(72) Inventors: Sven Krueger, Trossingen (DE); Josef-Benedikt Weiss, Rottweil (DE); Jian-Zoing Tan, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 392 days.

(21) Appl. No.: 17/965,024

(22) Filed: Oct. 13, 2022

(65) Prior Publication Data

US 2023/0034033 A1 Feb. 2, 2023

Related U.S. Application Data

(63) Continuation of application No. PCT/EP2021/059735, filed on Apr. 15, 2021.

(30) Foreign Application Priority Data

Apr. 17, 2020 (DE) ..................... 10 2020 110 516.9

(51) Int. Cl.
*A61B 17/70* (2006.01)
*A61B 17/86* (2006.01)

(52) U.S. Cl.
CPC ...... *A61B 17/7035* (2013.01); *A61B 17/7032* (2013.01); *A61B 17/8605* (2013.01); *A61B 17/8685* (2013.01)

(58) Field of Classification Search
CPC .................................................. A61B 17/7037
See application file for complete search history.

(56) References Cited

U.S. PATENT DOCUMENTS

| | | |
|---|---|---|
| 8,075,590 B2 | 12/2011 | Janowski et al. |
| 8,562,652 B2 | 10/2013 | Biedermann et al. |
| 2004/0225289 A1 | 11/2004 | Biedermann et al. |
| 2005/0131410 A1 | 6/2005 | Lin |
| 2005/0277928 A1 | 12/2005 | Boschert |

(Continued)

FOREIGN PATENT DOCUMENTS

| | | |
|---|---|---|
| DE | 10320417 A1 | 12/2004 |
| DE | 112004000251 T5 | 11/2006 |

(Continued)

OTHER PUBLICATIONS

Search Report received in International Application No. PCT/EP2021/059735 dated Aug. 12, 2021, with translation, 6 pages.

(Continued)

*Primary Examiner* — Andrew Yang
(74) *Attorney, Agent, or Firm* — Christopher A. Rothe; CM Law

(57) ABSTRACT

A surgical fixation system includes at least one anchoring element with an anchoring portion for anchoring to a bone and with a receiving portion for a stabilization element for connecting to a further anchoring element. The stabilization element is arrangeable and fixable in the receiving portion with a fixing element. The fixation system includes an abutment element arranged on the receiving portion. The receiving portion abuts against the anchoring portion for the placement of the stabilization element. The abutment element has at least one deformation region for deforming in dependence on a fixing force of the fixing element acting on the stabilization element.

20 Claims, 5 Drawing Sheets

(56) References Cited

U.S. PATENT DOCUMENTS

| | | |
|---|---|---|
| 2007/0233078 A1 | 10/2007 | Justis et al. |
| 2010/0057126 A1 | 3/2010 | Hestad |
| 2012/0253408 A1 | 10/2012 | Timm |
| 2014/0180346 A1 | 6/2014 | Abdou |
| 2017/0209184 A1 | 7/2017 | Fiechter et al. |
| 2018/0055543 A1 | 3/2018 | Courtney et al. |

FOREIGN PATENT DOCUMENTS

| | | |
|---|---|---|
| EP | 3174482 A0 | 6/2017 |
| JP | 2005169071 A | 6/2005 |
| JP | 2006525047 A | 11/2006 |
| WO | 2004071339 A2 | 8/2004 |
| WO | 2016016745 A1 | 2/2016 |

OTHER PUBLICATIONS

Written Opinion received in International Application No. PCT/EP2021/059735 dated Aug. 12, 2021, with translation, 17 pages.

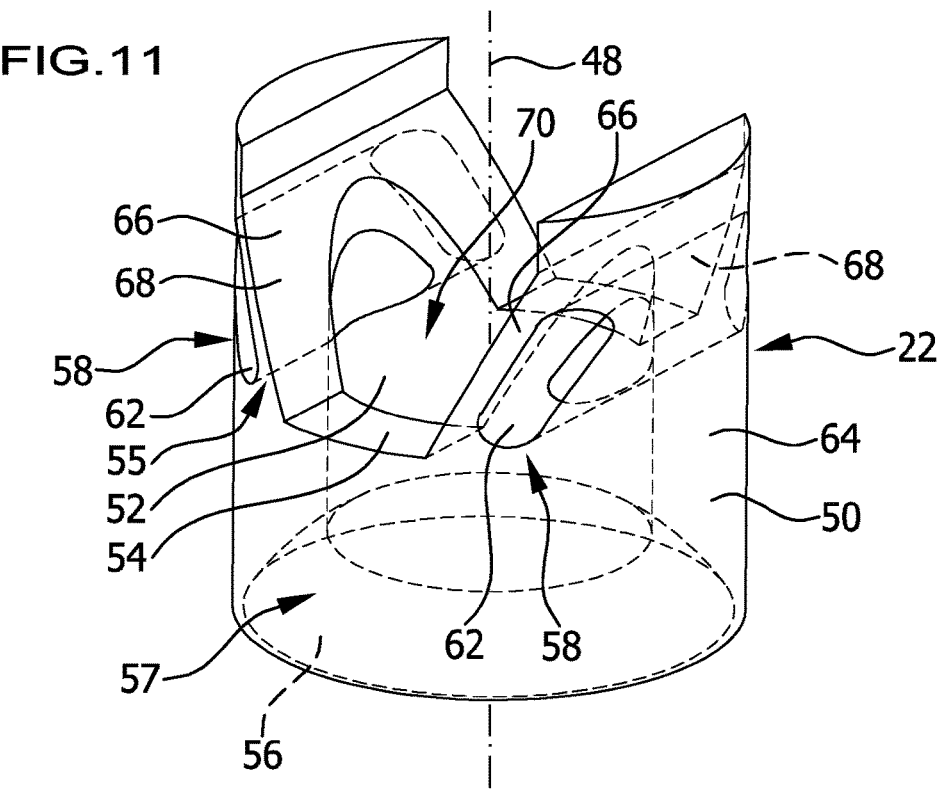
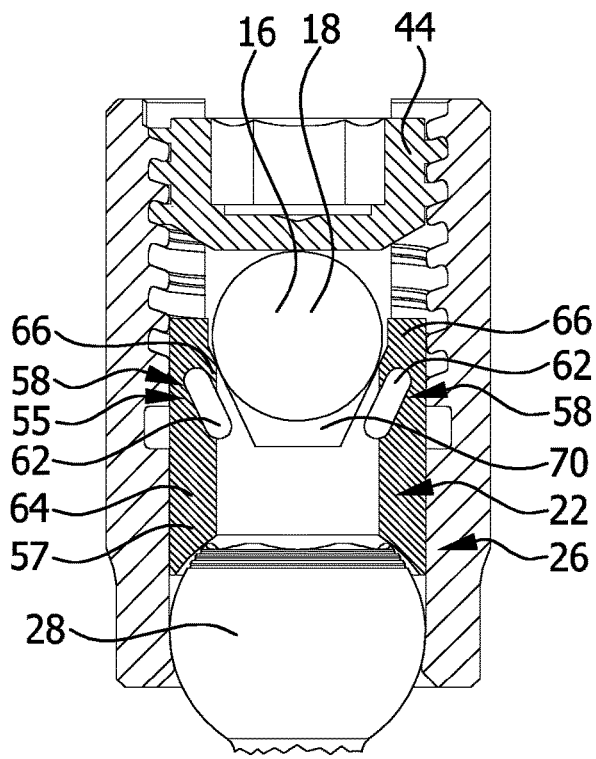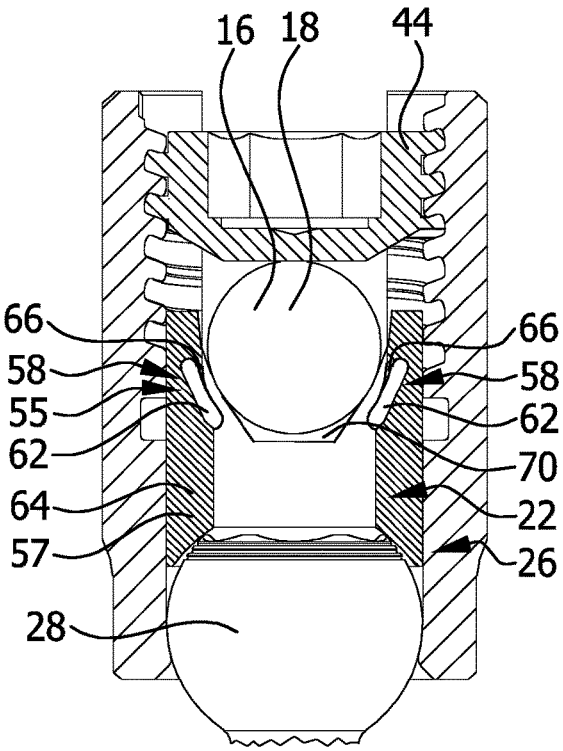

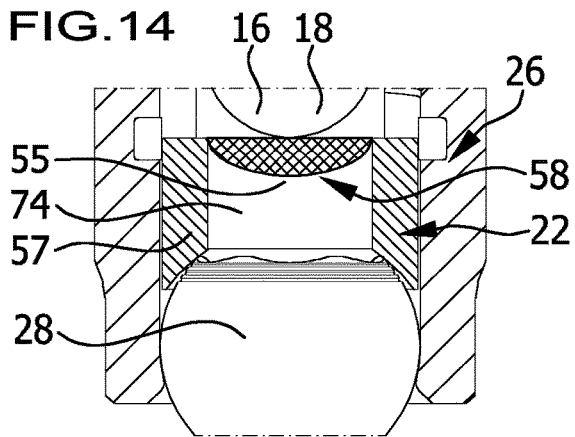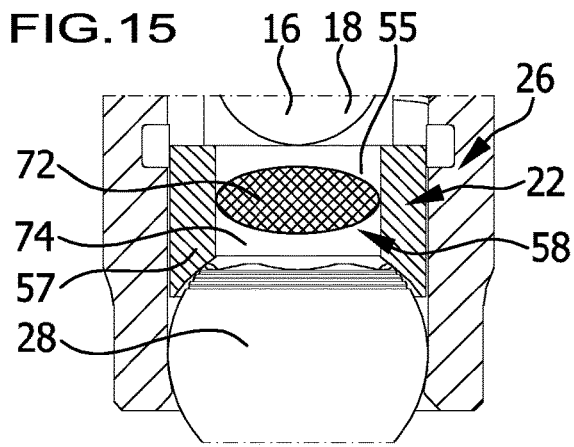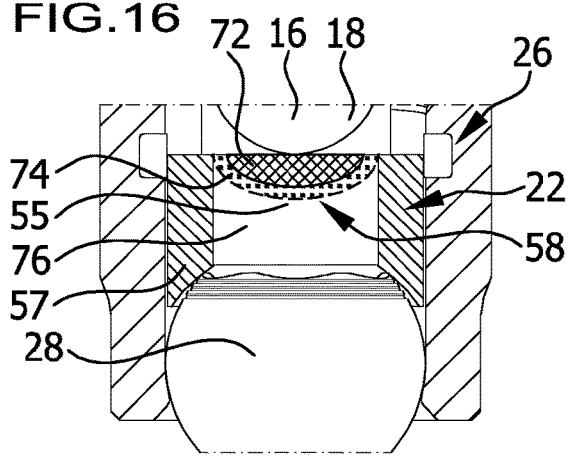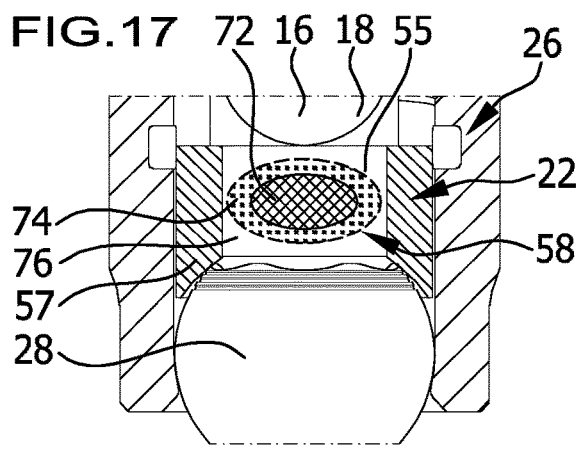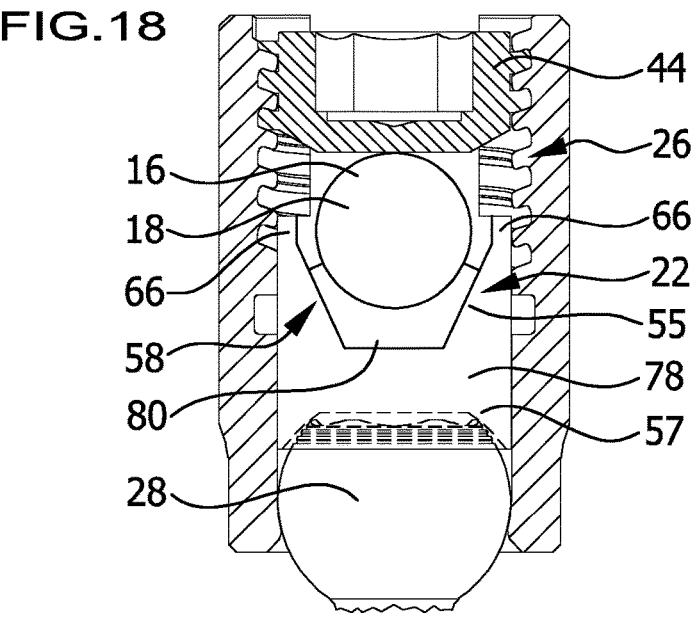

SURGICAL FIXATION SYSTEM

CROSS-REFERENCE TO RELATED APPLICATIONS

This application is a continuation of International Application No. PCT/EP2021/059735, filed on Apr. 15, 2021, and claims priority to German Application No. 10 2020 110 516.9, filed on Apr. 17, 2020. The contents of International Application No. PCT/EP2021/059735 and German Application No. 10 2020 110 516.9 are incorporated herein by reference in their entireties.

FIELD

The present disclosure relates to surgical fixation systems generally, and more specifically to a surgical fixation system, comprising at least one anchoring element with an anchoring portion for anchoring to a bone and with a receiving portion for a stabilization element for connecting to a further anchoring element, wherein the stabilization element is arrangeable in the receiving portion and is fixable therein by means of a fixing element.

BACKGROUND

A fixation system of that kind is used, for example, in the treatment of fractures in the spinal region. Here, anchoring elements may be provided, for example bone screws, in particular pedicle screws. A, for example, rod-shaped stabilization element can be inserted into the respective receiving portion of the bone screw and be clampingly fixed therein, for example by means of a screw element. In practice, the receiving portion may have, for example, two segments arranged at a distance from one another, between which an opening for the stabilization element is arranged. The segments may have, for example, an internal thread for screwing to an external thread of the screw element.

Depending on the treatment, it may be desirable or necessary, for example, to adapt stabilization elements of different qualities to the anchoring element. For example, the stabilization elements may have different materials and/or, in the case of rod elements, different diameters.

Described in US 2005/0277928 A1 is a fixation system in which a receiving portion with a substantially U-shaped abutment element is provided for adapting the anchoring element to different rod diameters. In this case, rod elements of different diameters can indeed be adapted better than in comparison to conventional fixation systems. However, the U-shaped abutment element leads to different distances of the rod element relative to the anchoring element. This is undesirable for the treatment. The quality of the abutment element leads further to line or point contacts of the rod element with the risk of an instable fixation in the receiving portion. Line and point contacts may lead to loosening effects and/or corrosion effects due to high fixing forces with the fixing element. The fixing of bent rod elements is often clinically appropriate, but it can lead to an unfavorable abutment of the rod element on the abutment element. This can result in constraining forces, loosening, break, and corrosion.

US 2005/0277928 A1 further describes that legs many be arranged on the abutment element, which can be spread relative to one another for inserting the stabilization element and then can be moved toward one another again after insertion. This makes it possible to temporarily fix the stabilization element in the receiving portion.

SUMMARY

In a first aspect of the present disclosure, a surgical fixation system is provided, which comprises at least one anchoring element with an anchoring portion for anchoring to a bone and with a receiving portion for a stabilization element for connecting to a further anchoring element. The stabilization element is arrangeable in the receiving portion and is fixable therein by means of a fixing element. The fixation system comprises an abutment element that is arranged on the receiving portion and abuts against the anchoring portion for the placement of the stabilization element. The abutment element has at least one deformation region for deforming in dependence on a fixing force of the fixing element acting on the stabilization element.

In a second aspect of the present disclosure, a surgical fixation system is provided, which comprises at least one anchoring element with an anchoring portion for anchoring to a bone and with a receiving portion for a stabilization element for connecting to a further anchoring element. The stabilization element is arrangeable in the receiving portion and is fixable therein by means of a fixing element. The fixation system comprises an abutment element that is arranged on the receiving portion and abuts against the anchoring portion for the placement of the stabilization element. The abutment element has at least one deformation region for deforming in dependence on a fixing force of the fixing element acting on the stabilization element. The abutment element is of sleeve-shaped configuration at least in sections and has on an end face an abutment region for the stabilization element. At least one deformation region is arranged beneath an abutment region of the abutment element for the stabilization element.

In a third aspect of the present disclosure, a surgical fixation system is provided, which comprises at least one anchoring element with an anchoring portion for anchoring to a bone and with a receiving portion for a stabilization element for connecting to a further anchoring element. The stabilization element is arrangeable in the receiving portion and is fixable therein by means of a fixing element. The fixation system comprises an abutment element that is arranged on the receiving portion and abuts against the anchoring portion for the placement of the stabilization element. The abutment element has at least one deformation region for deforming in dependence on a fixing force of the fixing element acting on the stabilization element. The abutment element comprises two or more deformation portions, which comprise or are made of different materials with respect to their deformability. The at least one deformation region is formed as a result of the materially different quality of the two or more deformation portions.

BRIEF DESCRIPTION OF THE DRAWING FIGURES

The foregoing summary and the following description may be better understood in conjunction with the drawing figures, of which:

FIG. 11 shows a perspective depiction of a different abutment element for the stabilization element;

FIGS. 12 and 13 show partial depictions corresponding to FIGS. 3 and 4, wherein the abutment element from FIG. 11 is used; and FIGS. 14 to 18 show a respective partial depiction corresponding to FIG. 3, wherein in each case different abutment elements are used.

DETAILED DESCRIPTION

Figure 1:
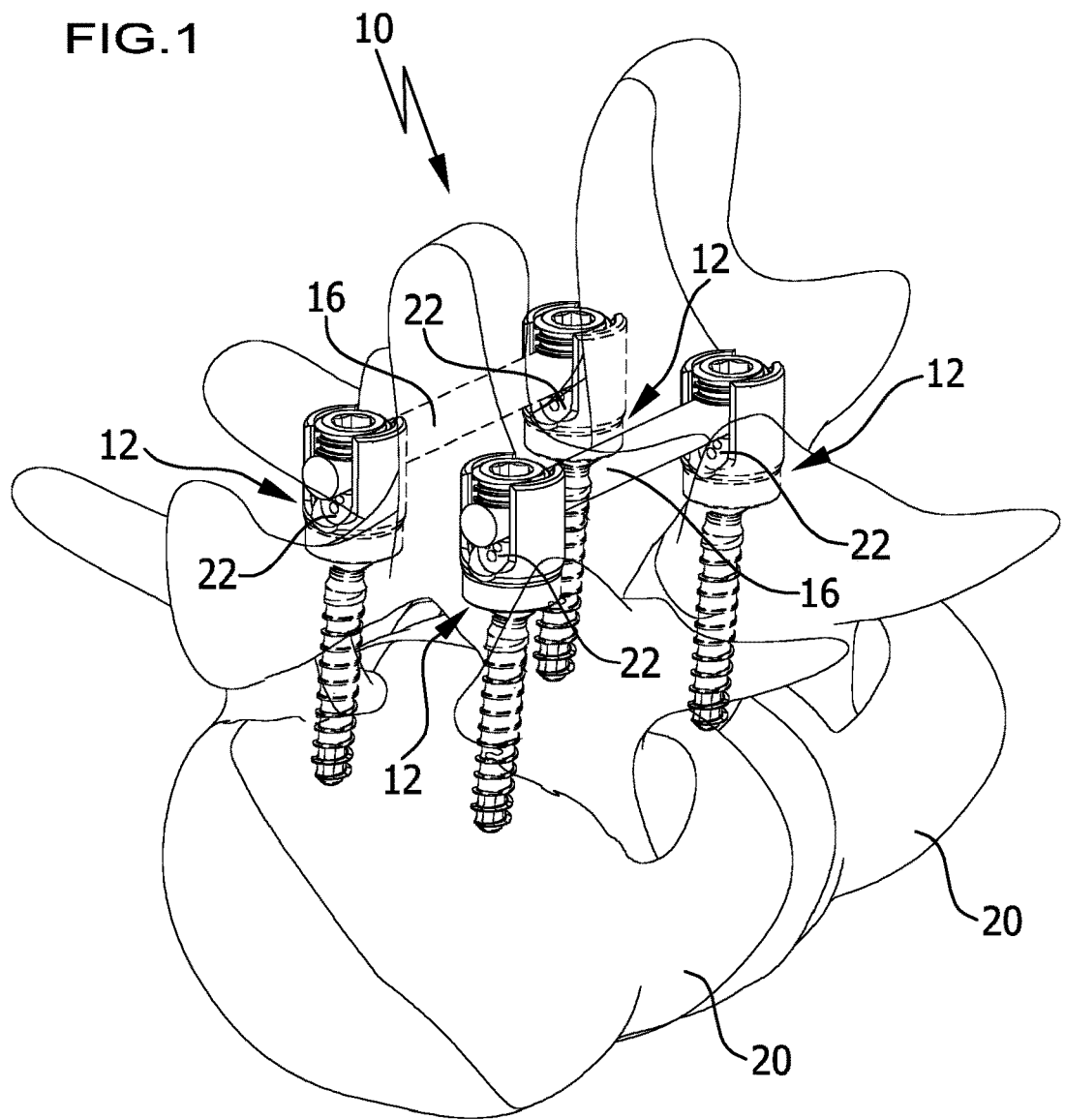
FIG. 1 shows a schematic perspective view of a fixation system in accordance with the present disclosure for connecting two vertebrae to one another.

Although the present disclosure is illustrated and described herein with reference to specific embodiments, the present disclosure is not intended to be limited to the details shown. Rather, various modifications may be made in the details without departing from the present disclosure.

The present disclosure relates to a surgical fixation system, comprising at least one anchoring element with an anchoring portion for anchoring to a bone and with a receiving portion for a stabilization element for connecting to a further anchoring element, wherein the stabilization element is arrangeable in the receiving portion and is fixable therein by means of a fixing element, wherein the fixation system comprises an abutment element that is arranged on the receiving portion and abuts against the anchoring portion for the placement of the stabilization element, wherein the abutment element has at least one deformation region for deforming in dependence on a fixing force of the fixing element acting on the stabilization element.

In the fixation system in accordance with the present disclosure, it is possible to fix the stabilization element to the receiving portion by way of the fixing element with a fixing force, in particular a clamping force. An abutment element is provided on the receiving portion, which can be deformed at least one deformation region as a result of the fixing force. Preferably a defined deformation of the abutment element at the at least one deformation region can be achieved. This makes it possible to better adapt different stabilization elements, which differ from one another, for example, with respect to their material and/or their geometry (for example diameter), to the receiving portion. At the same time, the abutment element abuts against the anchoring portion, such that preferably an improved seating of the stabilization element on the anchoring portion can be achieved. Preferably an anchoring element may hereby be used with a multitude of different stabilization elements, wherein preferably an identical distance from the anchoring element can be achieved. The fixation system therefore has a higher versatility. The provision of fixation systems for different treatments is greatly simplified. Preferably an equalization of the forces acting on the stabilization element can be achieved as a result of the deformation of the abutment element and/or a surface-to-surface abutment on the abutment element with, in particular, a reliable seating on the anchoring element. This enables a more reliable fixing of the stabilization element than with conventional fixation systems.

In a preferred embodiment of the present disclosure, provision may be made that the abutment element is formed separate from the receiving portion and is arranged in the receiving portion. This increases the versatility of the fixation system. For example, different abutment elements may be provided, which can selectively be positioned in the receiving portion in dependence on the treatment to be performed. In particular, here there is a possibility of a modular structure of the fixation system. By producing the receiving portion and the at least one abutment element separately, the respective advantages of these two components can be highlighted with a view to the best possible care.

In a different kind of advantageous embodiment, provision may be made that the receiving portion comprises or forms the abutment element. This enables, for example, a constructively simple production.

The abutment element is, in particular, squishable as a result of the fixing force of the fixing element.

Provision may be made that the abutment element is of elastically deformable configuration at least at the at least one deformation region.

Provision may be made that the abutment element is of plastically deformable configuration at least at the at least one deformation region.

In a preferred embodiment of the present disclosure, the abutment element may be in one piece.

It may prove to be advantageous if at least one deformation region is arranged at or beneath an abutment region of the abutment element for the stabilization element. The force of the fixing element may be directed, in particular, via the stabilization element to the abutment region, in particular support region, or the at least one deformation region of the abutment element located beneath.

Alternatively or in addition, at least one deformation region may be arranged at or laterally next to a lateral abutment region for the stabilization element. For example, the abutment element has lateral support members for the stabilization element, which each comprise an abutment region. An adaptation of the abutment element to the stabilization element can take place as a result of the deformation of the support member.

In a preferred embodiment of the present disclosure, provision may be made that the abutment element comprises a first abutment element portion facing toward the stabilization element and a second abutment element portion facing toward the anchoring portion. It may be favorable, in particular, if the first abutment element portion comprises or forms the at least one deformation region and has, at least in sections, a higher deformability as a result of the fixing force than the second abutment element portion. By way of the first abutment element portion, as mentioned, an adaptation to the stabilization element and preferably a plurality of stabilization elements may take place. Here, the at least one deformation region can deform in dependence on the fixing force to the size and/or shape of the stabilization element and the abutment element can thereby adapt to the stabilization element. At the second abutment element portion, the abutment element has a lesser deformability than at the first abutment element portion. This can presently be understood to mean, in particular, that the abutment element portion is "harder" at the second abutment element portion than at the first abutment element portion. A reliable seating, preferably by force-fit and/or positive engagement, on the anchoring portion can thereby be achieved.

The abutment element portions may, for example, be made of different materials or, if made from the identical material, have a different quality with respect to deformability.

The abutment element portions may, for example, be formed separate from one another and joined together. Alternatively, provision may be made that the abutment element portions are formed with one another, in particular in one piece.

For example a portion boundary, which is discrete with respect to the deformability of the abutment element, is provided between the first abutment element portion and the second abutment element portion. Here, for example, there may be a step-wise change in the deformability at the abutment element portion.

The section boundary is oriented, for example, transversely and, in particular, perpendicularly to a fixing direction of the fixing element in the direction of the anchoring portion.

In a preferred embodiment, provision may be made that a transition portion with respect to the deformability of the abutment element is present, via which the first abutment element portion and the second abutment element portion merge with one another.

In a preferred embodiment, the at least one deformation region may have an extent in parallel to an abutment region of the abutment element for the stabilization element.

Provision may be made that the at least one deformation region is arranged or formed symmetrically on the abutment element with respect to a symmetry plane containing an axis of the receiving portion. In particular, the abutment element may hereby be positioned coaxially to the receiving portion. The symmetry plane is, for example, a midplane of the receiving portion. Due to a symmetrical arrangement of the deformation region, an equalization of the fixing forces can advantageously be achieved.

It is favorable if the at least one deformation region is formed by or comprises at least one material recess on the abutment element.

The material recess is, for example, a recess on a surface of the abutment element, wherein the abutment element is deformable at the rim of the recess. Here, provision may advantageously be made that the stabilization element engages into the recess in a positive-locking manner.

In a preferred embodiment of the present disclosure, the material recess is or comprises a through-opening of the abutment element. By forming one and, for example, a plurality of through-opening(s), a structurally simple implementation of the present disclosure can be achieved. For example, the abutment element is squished under the effect of the fixing force, the through-openings being variable in shape.

The through-opening may have, for example, a circular, elliptical, oval, round, elongate hole-shaped, or a non-round cross section. "Round" may presently be understood to mean, in particular, non-angular.

Provision may be made that the material recess has an extent along the stabilization element arranged in the receiving portion. The stabilization element may have a preferred direction as a result of the configuration of the receiving portion, in particular with two segments arranged at a distance from one another. The material recess may extend along, in particular, this preferred direction. This enables an improved adaptation of the abutment element to the geometry of the stabilization element with a view to a most advantageous deformation.

Provision may be made that the material recess has an extent radial to an axis defined by the abutment element.

In a preferred embodiment of the present disclosure, the material recess is a cavity that is formed in the receiving element and is enclosed on all sides.

It may be advantageous if the abutment element comprises two or more deformation portions, which comprise materials that are different with respect to their deformability or are made of different materials, wherein the at least one deformation region is formed as a result of the materially different quality of the two or more deformation portions.

For example, two deformation portions with differing deformability adjoin one another. As a result of the application of force, the abutment element can deform at the softer deformation portion and/or in the transition portion between the softer and the less soft deformation portion.

The two or more deformation portions may be formed separate from one another and be deformation portions of the abutment element that are joined to one another.

Alternatively, provision may be made that the two or more deformation portions are formed in one piece with one another.

It may be advantageous if a first deformation portion is provided, which is surrounded at least partially by at least one second deformation portion, wherein the deformability of the first deformation portion is greater than the deformability of the at least one second deformation portion. In particular, the second deformation portion may completely surround the first deformation portion.

In a preferred embodiment, three or more deformation portions may be provided, wherein the deformability of a respective deformation portion that at least partially surrounds a further deformation portion, is lesser than the deformability of the surrounded deformation portion.

Provision may be made that the deformation portions of differing deformability directly adjoin one another, such that it results in a discrete, step-wise change in deformability on the abutment element.

Alternatively, provision may be made that a transition portion is present between the deformation portions of differing deformability, such that the deformability changes in steps and, in particular, continuously.

It may be favorable if the abutment element comprises a plurality of deformation regions, in particular with a plurality of material recesses.

Here, provision may be made, in particular, that two or more identically configured deformation regions are provided.

Alternatively or in addition, two or more differently configured deformation regions may be provided.

Two or more through-openings on the abutment element may, for example, be arranged and oriented in parallel to one another.

Provision may be made that a plurality of through-openings are arranged staggered relative to one another "in gaps".

It may prove to be favorable if two deformation regions are provided, which are arranged on the abutment element at a distance from one another and in alignment with one another.

For example, the abutment element, for example in the case of a sleeve-shaped configuration, has two diametrically opposed deformation regions. The deformation regions, for example formed by through-openings or deformation portions of differing deformability, are preferably in alignment with one another. The direction of alignment advantageously corresponds to the direction of extent of the stabilization element in the receiving portion.

The abutment element is preferably of sleeve-shaped configuration at least in sections, wherein it has an abutment region for the stabilization element on an end face. The end face may be located opposite a further end face, by way of which the abutment element can abut on the anchoring portion.

For example, the first abutment element portion mentioned above on an end face may comprise or form the abutment region.

In a preferred embodiment, the abutment element may comprise two support members arranged at a distance from one another, which laterally delimit a tapering depression, wherein the stabilization element is positionable in the depression between the support members. The stabilization element can be laterally supported by the support members and thereby be particularly advantageously fixed in the receiving portion.

A deformation region is preferably arranged at least on one support member, preferably on both support members.

The abutment element may preferably be oriented or orientable coaxially to the receiving portion and/or to the anchoring portion.

It is favorable if the anchoring portion and the abutment element comprise abutment regions that are adapted to one another and, in particular, are spherical cup-shaped at least in sections. For example, the anchoring element is a polyaxial screw with a spherical anchoring portion. The abutment element adapted in this regard can thereby abut, preferably in a positive-locking manner, on the abutment region of the anchoring portion and adopt a defined position relative to the anchoring portion.

For example, the aforementioned second abutment element portion may comprise or form the abutment region on an end face. A reliable seating of the abutment element with a preferably optimized fit on the anchoring portion can be achieved by way of the abutment region.

The abutment element is favorably arranged in the receiving portion in a positive-locking manner. For example, the abutment element is positioned in a positive-locking manner between two segments of the receiving portion arranged at a distance from one another.

The fixation system may comprise, e.g., two or more anchoring elements. The anchoring elements may preferably be of identical configuration.

The fixation system preferably comprises two or more abutment elements. Here, at least two identically configured and/or at least two differently configured abutment elements may be provided.

The fixation system preferably comprises at least one stabilization element, in particular a plurality of stabilization elements. At least two stabilization elements may be of identical configuration. Alternatively or in addition, at least two stabilization elements are of differing configuration.

The fixation system preferably comprises at least one fixing element, in particular a plurality of fixing elements. At least two fixing elements may be of identical configuration. Alternatively or in addition, at least two fixing elements are of differing configuration.

The at least one anchoring element is, for example, a bone screw. The bone screw may be a monoaxial screw. Alternatively, the bone screw may be a polyaxial screw, in which the receiving portion is pivotable relative to the anchoring portion.

The at least one stabilization element is preferably a rod element.

The at least one fixing element is preferably a screw element that can be screwed to the receiving portion.

Used as materials for the abutment element are, for example, $Ti_6Al_4V$, titanium, PEEK, or a CoCr alloy. Combinations of the preceding materials are conceivable.

In particular, at the deformation region the abutment element has, for example, an elasticity modulus of about 50,000 to 150,000 MPa, for example about 100,000 to 120,000 MPa for $Ti_6Al_4V$. The elasticity modulus may be, for example, about 2,000 to 6,000 MPa (for example 3,000 to 4,000 MPa) for PEEK and, for example, about 200,000 to 300,000 MPa for CoCr, preferably about 230,000 to 270,000 MPa.

A fixing force of the fixing element acting on the stabilization element may be about 3 kN to about 7 kN in the case of spinal fixation systems in the lumbar region and about 0.8 kN to 2.5 kN for a spinal fixation system in the cervical region.

By contrast, the forces on the stabilization element in the implanted state are typically significantly lower. For example, axial forces of up to about 300 N on the stabilization element arise. A bending moment may be, e.g., up to about 8 Nm.

A deformation of the abutment element in accordance with the present disclosure may be, for example, approximately in the range of 0.1 mm to 3 mm, preferably between 0.2 mm and 1.5 mm.

The present disclosure further relates to a surgical fixation system, comprising at least one anchoring element with an anchoring portion for anchoring to a bone and with a receiving portion for a stabilization element for connecting to a further anchoring element, wherein the stabilization element is arrangeable in the receiving portion and is fixable therein by means of a fixing element, wherein the fixation system comprises an abutment element that is arranged on the receiving portion and abuts against the anchoring portion for the placement of the stabilization element, wherein the abutment element has at least one deformation region for deforming in dependence on a fixing force of the fixing element acting on the stabilization element,
   wherein the abutment element is of sleeve-shaped configuration at least in sections and has on an end face an abutment region for the stabilization element, and
   wherein at least one deformation region is arranged beneath an abutment region of the abutment element for the stabilization element.

The present disclosure further relates to a surgical fixation system, comprising at least one anchoring element with an anchoring portion for anchoring to a bone and with a to receiving portion for a stabilization element for connecting to a further anchoring element, wherein the stabilization element is arrangeable in the receiving portion and is fixable therein by means of a fixing element, wherein the fixation system comprises an abutment element that is arranged on the receiving portion and abuts against the anchoring portion for the placement of the stabilization element, wherein the abutment element has at least one deformation region for deforming in dependence on a fixing force of the fixing element acting on the stabilization element,
   wherein the abutment element comprises two or more deformation portions, which comprise or are made of different materials with respect to their deformability, wherein the at least one deformation region is formed as a result of the materially different quality of the two or more deformation portions.

FIG. 1 shows a fixation system in a preferred embodiment of the present disclosure, denoted as a whole with the reference numeral 10. For example, anchoring elements 12 in the form of bone screws 14 are provided in the fixation system 10.

The fixation system 10 comprises four thereof, at least one bone screw 14 being provided in accordance with the present disclosure.

Furthermore, the fixation system 10 comprises at least one stabilization element 16, wherein presently two stabilization elements 16, configured as rod elements 18, are provided. Two respective bone screws 14 are connected to one another by way of a rod element 18.

The fixation system 10 serves to stabilize bones, presently adjacent vertebral bodies 20. For this purpose, the bone screws 14 are in particular pedicle screws.

The four bone screws 14 and the two rod elements 18 are each of identical configuration. Only one of the bone screws 14 and one rod element 18 will be described in the following.

Figure 2:
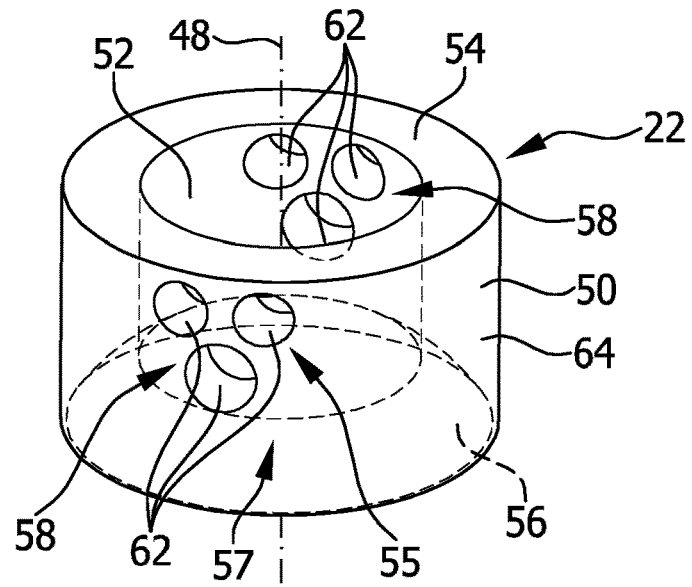
FIG. 2 shows a perspective depiction of an abutment element of the fixation system from FIG. 1.
Figure 4:
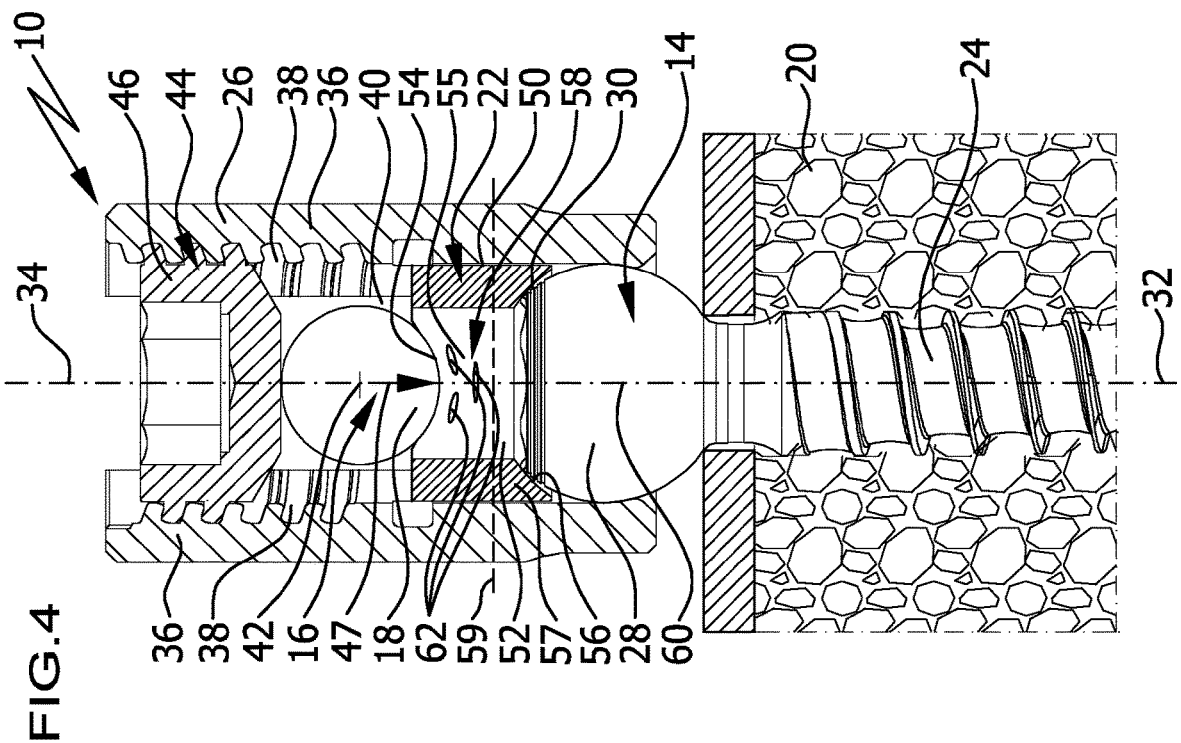
FIG. 4 shows a depiction corresponding to FIG. 3, wherein the stabilization element is acted upon with a fixing force by means of the fixing element and is thereby clampingly fixed.
Figure 3:
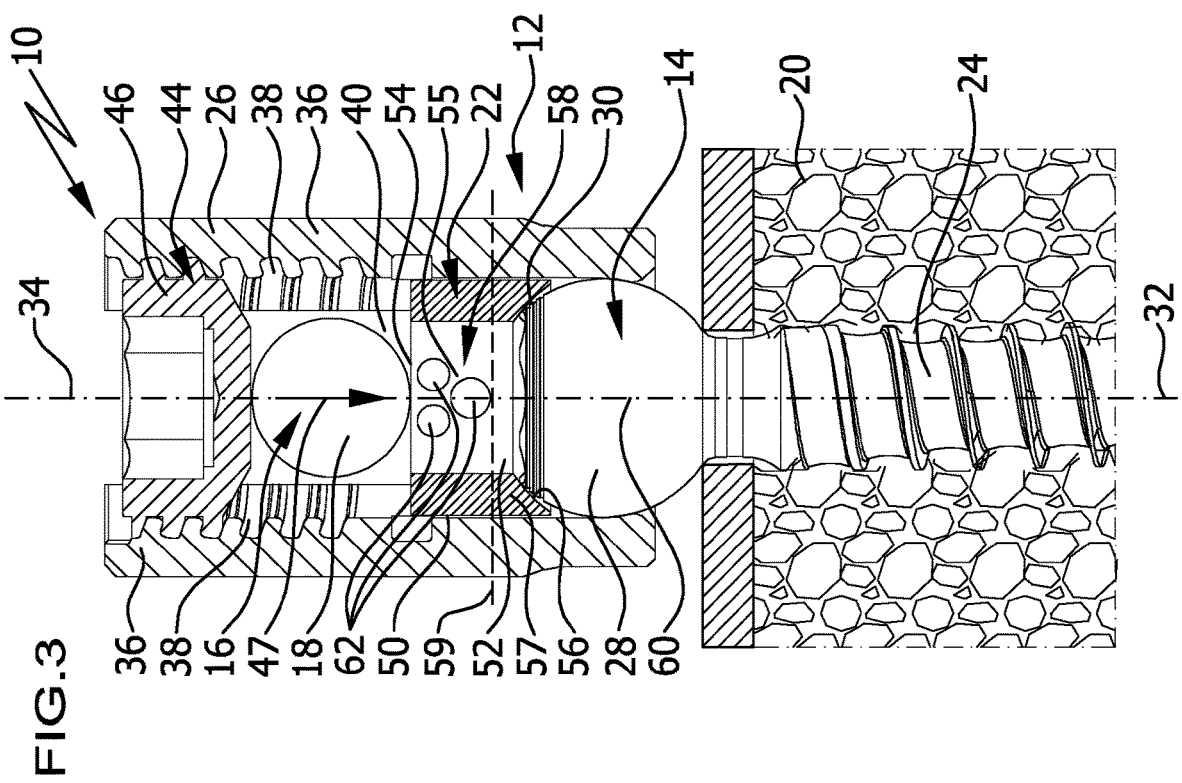
FIG. 3 shows a cut view of the fixation system from FIG. 1 in a partial depiction, wherein a stabilization element abuts against the abutment element according to FIG. 2 and cannot yet be acted upon with a fixing force by a fixing element.

The fixation system 10 further comprises at least one abutment element 22. A preferred embodiment of the abutment element 22 is depicted in FIGS. 2 to 4. Favorably, each bone screw 14 is associated with an abutment element 22.

Provision may be made, in particular, that the abutment elements 22 are of identical configuration.

As can be seen, in particular, in FIGS. 3 and 4, the bone screw 14 comprises an anchoring portion 24 for anchoring in the bone and a receiving portion 26 for the rod element 18. The bone screw 14 is presently a polyaxial screw in which the receiving portion 26 is pivotable relative to the anchoring portion 24. For this purpose, the anchoring portion 24 comprises a head 28 that, in the present case, is spherical. The head 28 defines an abutment region 30 that is spherical cup-shaped at least in sections.

The anchoring portion 24 defines an axis 32. The receiving portion 26 defines an axis 34. In the relative orientation of the anchoring portion 24 and the receiving portion 26 depicted in the drawing, the axes 32, 34 coincide.

The receiving portion 26 has two segments 36 arranged at a distance from one another. An internal thread 38 is arranged on a respective segment 36.

Formed between the segments 36 is a through-opening 40, through which the rod element 18 can be passed. A direction of extent of the rod element 18 preferably corresponds to an axis 42 of the through-opening 40.

For fixing the rod element 18 in the receiving portion 26, the fixation system 10 comprises a respective fixing element 44. The fixing element 44 is presently a screw element 46. The screw element 46 can be screwed to the threads 38 of the segments 36. This makes it possible to act upon the rod element 18 in a fixing direction 47 with a fixing force directed toward the anchoring portion 24.

In the present case, the abutment element 22 is provided for supporting the rod element 18 relative to the anchoring portion 24. Here, the abutment element 22 and the screw element 46 are arranged on opposing sides of the rod element 18.

The abutment element 22 is formed separate from the receiving portion 26 and is arranged in the receiving portion 26. Presently, the abutment element 22 is dimensioned such that it is positioned in a positive-locking manner between the segments 36 in the through-opening 40. An outer contour of the abutment element 22 is hereby preferably adapted to an inner contour of the segments 36. Presently, these respective contours are circular or circular arc-shaped. This makes it possible to position the abutment element 22 in the receiving portion 26 so as to be immovable in a plane transverse and, in particular, perpendicular to the axis 34.

As can further be seen in FIGS. 2 to 4, the abutment element 22 in the present example is of sleeve-shaped configuration with a central through-opening and thereby defines an axis 48. In the receiving portion 26 the abutment element 22 is arranged and oriented coaxially thereto, wherein the axes 34 and 48 are in alignment with one another. Depending on the relative orientation of the anchoring portion and the receiving portion 26, the abutment element 22 may also be arranged coaxially to the anchoring portion 24.

The abutment element 22 presently comprises an outer peripheral surface 50, an inner peripheral surface 52, an abutment region 54 on an end face facing toward the rod element 18, and an abutment region 56 on an end face facing toward the head 28.

The abutment element 22 comprises a first abutment element portion 55 and a second abutment element portion 57. The first abutment element portion 55 faces toward the rod element 18 and forms the abutment region 54 on the end face. The second abutment element portion 57 faces toward the anchoring portion 24, in particular the head 28 thereof. On the end face, the second abutment element portion 57 forms the abutment region 56.

Relative to the fixing direction 47, the first abutment element portion 55 is arranged proximally with respect to the rod element 18 and the second abutment element portion is arranged distally with respect to the rod element 18. The opposite applies with respect to the anchoring portion 24, in particular the head 28.

For the purposes of explanation, a fictive dividing plane between the abutment element portions is drawn in by means of a dashed line 59 in FIGS. 3 and 4. The abutment element portions 55 and 57 also presently merge into one another, in particular with respect to their deformability, along the fixing direction 47. A corresponding transition portion is not depicted separately in the drawing.

In a different advantageous embodiment, provision could be made that a discrete portion boundary, in particular with respect to its deformability, is provided between the abutment element portions 55 and 57. The portion boundary is, for example, oriented transversely and, in particular, perpendicularly to the fixing direction 47 (presently transversely and, in particular, perpendicularly to the drawing plane).

The abutment region 56 is of spherical cup-shaped configuration and is adapted in its shape to the abutment region 30. When the receiving portion 26 is pivoted relative to the anchoring portion 24, as long as the fixing element 44 is unfixed, the abutment element 22 is thereby pivoted too, the abutment region 56 always remaining in surface-to-surface contact with the head 28.

The abutment region 54 is presently of planar configuration and is formed by the annular end face of the abutment element 22. The rod element 18 can abut against and, in particular, rest on the abutment region 54 (FIGS. 3 and 4).

The abutment element 22 comprises at least one deformation region 58. Presently, two deformation regions 58 are provided, which are arranged on portions of the abutment element 22 that are diametrically opposed to one another relative to the axis 48.

In the case of the abutment element 22, the first abutment element portion 55 comprises the deformation region 58 or forms the at least one deformation region 58. By contrast, the second abutment element portion 57 presently comprises or forms no deformation region.

As a result of the at least one deformation region 58 (presently two deformation regions), the first abutment element portion 55 has a higher deformability than the second abutment element portion 57. The deformability is effected due to the fixing force of the fixing element 44 and enables an adaptation of the abutment element 22 to the rod element 18. This is explained in the following.

By contrast, the second abutment element 57 is "harder" or "stiffer" than the first abutment element portion 55. This enables a reliable seating on the head 28, thereby ensuring, for example, the aforementioned surface-to-surface contact by way of the abutment region 56.

As explained above, the second abutment element portion 57 may be, in particular, non-deformed or substantially non-deformed in the case of the fixing forces that typically occur with the fixing element 44.

By way of the aforementioned transition portion, the deformability may, for example, gradually decrease from the first abutment element portion 55 to the second abutment element portion 57. If, as mentioned above, a portion boundary is provided, for example, a step-wise change in the deformability from the first to the second abutment element portion 55, 57 may arise.

The deformation regions 58 are of symmetrical configuration relative to one another with respect to a first plane containing the axes 34, 48. In FIGS. 3 and 4, this plane extends in the drawing plane. Moreover, the deformation regions 58 are of symmetrical configuration in themselves with respect to a plane containing the axes 34, 48. This is a plane 60 perpendicular to the drawing plane in FIGS. 3 and 4, wherein the symmetry plane 60 is a midplane of the receiving portion 26 in the intended use of the fixation system 10.

The deformation regions 58 are arranged beneath the abutment region 54.

At least one material recess is present on a respective deformation region 58. Presently, each deformation region 58 comprises three material recesses, configured as through-openings 62 of the abutment element 22. The through-openings 62 have a round and, in particular, circular cross section.

Of these, two through-openings 62 are of identical configuration and are arranged symmetrically to one another relative to the plane 60. A third through-opening 62 is arranged staggered in a gap between these two through-openings 62 and is symmetrical in itself with respect to the plane 60. The last-mentioned through-opening 62 has a greater diameter than the first-mentioned through-openings 62.

The through-openings 62 on the deformation regions 58 opposite one another with respect to the axis 48 are each in alignment. The through-openings 62 are hereby each oriented in the direction of extent of the rod element 18. Preferably, the through-openings 62 are oriented in parallel to the axis 42.

The through-openings 62 presently run in parallel to a plane defined by the abutment region 54.

In the use of the fixation system 10, the rod element 18 is acted upon by the screw element 46 with a fixing force directed at the abutment element 22 and via same to the head 28 (FIG. 4). The fixing force leads to a deformation of the abutment element 22 at the deformation regions 58. A targeted deformation can preferably be achieved here.

It is possible by way of the deformation to adapt rod elements 18 of different qualities, in particular different materials and/or different diameters, to the bone screw 14. Separate bone screws 14 are not necessary. The versatility of the fixation system 10 is thereby increased.

As a result of the deformation of the abutment element 22, in particular, a surface-to-surface contact region between the rod element 18 and the abutment element 22 can be achieved. This promotes the equalization of the pressing and helps to avoid point contacts and line contacts. In this way, a reliable fixing of the rod element 18 is ensured. Possible corrosion is counteracted.

A reliable fit with respect to the head 28 is ensured by way of the abutment element portion 57 that is stiffer compared to the abutment element portion 55.

The deformation of the abutment element 22 may be plastic or elastic.

The abutment element 22 is preferably formed in one piece.

Reference is made to the preceding statements with regard to advantageous materials and the forces occurring in the use of the fixation system 10.

Further preferred embodiments of the present disclosure are discussed in the following with reference to FIGS. 5 to 18. Here, a different abutment element is used in place of the abutment element 22 depicted in FIGS. 1 to 4. Depicted is the use in each case with the bone screw 14 and the rod element 18.

The advantages described above can also be achieved using the abutment elements described in the following, such that reference can be made to the preceding statements in this regard. The depiction of FIGS. 5 and 6, 7 and 8, 9, and 10, and 12 and 13 corresponds to the depiction in FIGS. 3 and 4 in a partial view.

The depictions of FIGS. 14 to 18 correspond to the depiction according to FIG. 3 in a partial view. Here, the respective abutment element 22 is not acted upon with the fixing force, but instead is shown in the state unsubjected to force for a clearer view.

The embodiments depicted in FIGS. 5 to 18 each have an abutment element 22, which preferably have the abutment element portions 55 and 57 for the rod element 18 or for the anchoring portion 24, in particular the head 28. Here, in each case the deformability at the abutment element portion 55 is higher than at the abutment element portion 57, wherein the abutment element portion 55 comprises or forms at least one respective deformation region 58.

Figure 5:
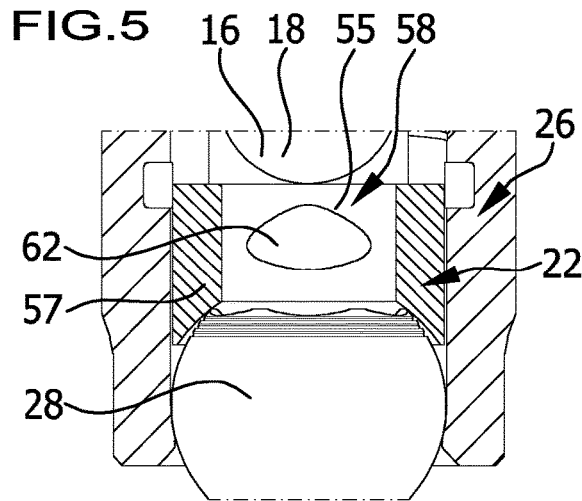
FIGS. 5 and 6 show partial depictions corresponding to FIGS. 3 and 4, wherein a different abutment element is used.
Figure 6:
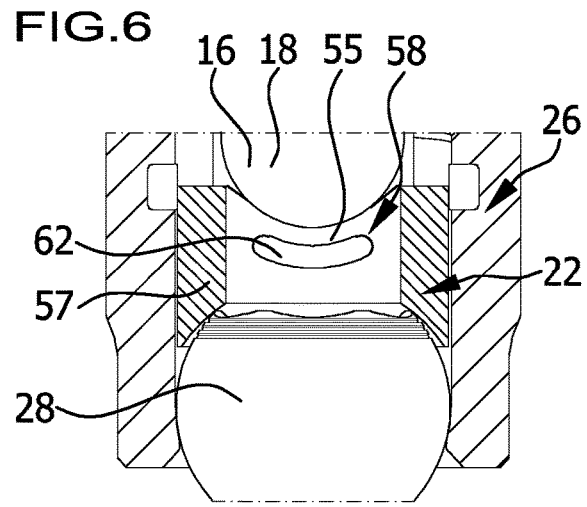

The abutment element 22 according to FIGS. 5 and 6 has only one through-opening 62 at the respective deformation region 58. In the state unsubjected to force, the through-opening 62 is approximately of the form of a rounded off, widened equilateral triangle, approximately of the form of a Reuleaux triangle. In the state subjected to load, the through-opening 62 is, for example, arcuate, in dependence on the fixing force.

In the embodiments depicted in FIGS. 7 to 10, too, only one respective through-opening 62 of the deformation region 58 is provided.

Figure 7:
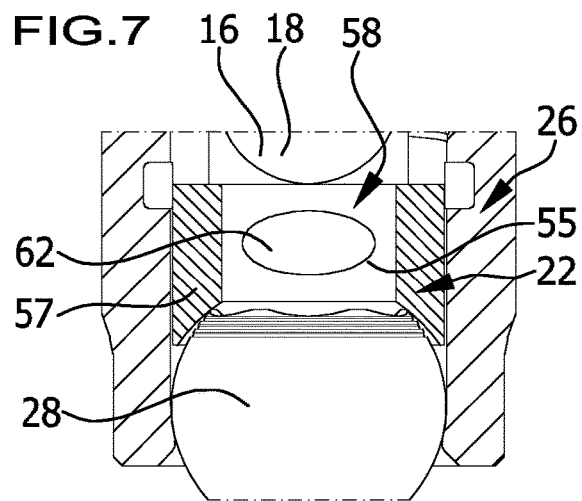
FIGS. 7 and 8 show partial depictions corresponding to FIGS. 3 and 4, wherein a different abutment element is used.
Figure 8:
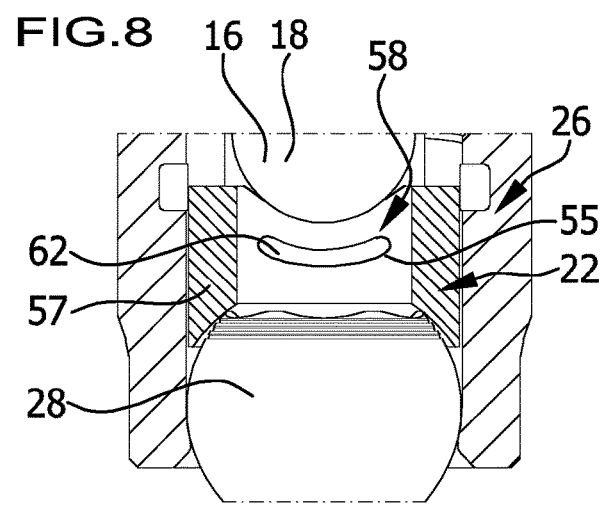

In the embodiment according to FIGS. 7 and 8, the through-opening 62 is elliptical in the state unsubjected to force. In the state subjected to load, the through-opening 62 is, for example, arcuate, in dependence on the fixing force.

Figure 9:
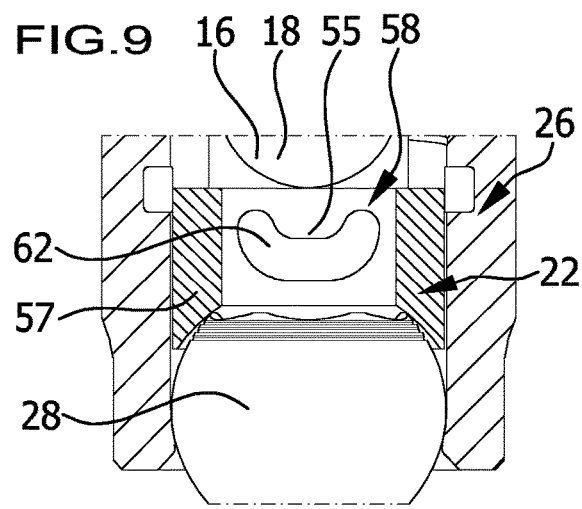
FIGS. 9 and 10 show partial depictions corresponding to FIGS. 3 and 4, wherein a different abutment element is used.
Figure 10:
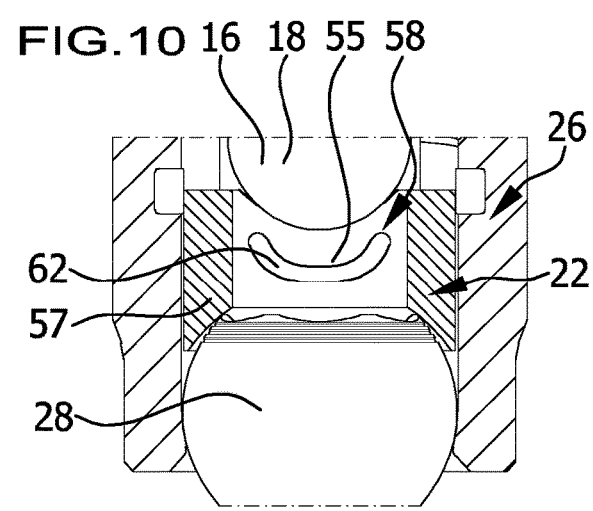

In the embodiment according to FIGS. 9 and 10, the through-opening 62 is approximately C-shaped in the state unsubjected to force, in each case with ends of the "C" pointing in the direction toward the rod element 18. In the state subjected to force, the through-opening 62 has approximately the form of a U with legs pointing in the direction toward the rod element 18.

FIG. 11 shows an embodiment of the abutment element 22, which comprises a sleeve-shaped portion 64. Projecting from the portion 64 are two support members 66 located opposite one another with respect to the axis 48. A respective support member 66 forms a lateral abutment region 68 for the rod element 18.

A deformation region 58 is arranged on a respective support member 66. The deformation region 58 has a respective through-opening 62 with an elongate hole-shaped cross section that extends in parallel to the axis 42.

Arranged between the support members 66 is a depression 70 that tapers in the insertion direction of the rod element 18. It is ensured by way of the depression 70 that the rod element 18 is centered relative to the receiving portion 26.

The rod element 18 can contact the abutment regions 68. A contact of the rod element 18 with the abutment region 54 (not shown) may also be provided.

In the embodiments described thus far, the deformation region 58 comprises at least one respective material recess, in particular in the form of the through-opening 62.

Deviating from this, the respective abutment element 22 depicted in FIGS. 14 to 18 has no material recess. Instead, the respective deformation region 58 is formed by way of deformation portions of the abutment element 22 with differing deformabilities.

In the depictions according to FIGS. 14 to 17, two respective deformation regions 58 located opposite one another with respective to the axis 48 are provided. Of these, only one deformation region 58 is shown in the drawing.

The abutment element 22 according to FIG. 14 comprises a first deformation portion 72 and a second deformation portion 74. The second deformation portion 74 is formed by the sleeve-shaped base body of the abutment element 22, from which a concave recess is cut out on the side facing toward the rod element 18. The recess is filled by the first deformation portion 72.

The deformability of the first deformation portion 72 is higher than the deformability of the second deformation portion 74. When force is applied, the deformation element 22 thereby deforms more at the first deformation portion 72 than at the second deformation portion 74 for adapting the rod element 18.

Two deformation portions 72, 74 are provided in the case of the abutment element 22 according to FIG. 15, too.

While the second deformation portion 74 surrounds the first deformation portion 72 only in sections in the embodiment according to FIG. 14, the deformation portion 72 is completely surrounded in the peripheral direction by the deformation portion 74 in the embodiment according to FIG. 15. The deformation portion 72 may, however, reach, for example, from the outer peripheral surface 50 to the inner peripheral surface 52.

The deformation portion 72 has an approximately elliptical shape in cross section.

The embodiment according to FIG. 16 differs from the embodiment according to FIG. 14 in that the first deformation portion 72 is arranged within a recess of the second deformation portion 74, which itself is arranged within a recess of the base body of the abutment element 22 forming a third deformation portion 76. The second deformation portion 74 forms a sort of transition portion from the first deformation portion 72 to the third deformation portion 76, wherein this deformation portion 76 corresponds to the second deformation portion 74 in the embodiment according to FIG. 14.

In particular, the deformability at the second deformation portion 74 is lesser than at the first deformation portion 72, and the deformability of the third deformation portion 76 is lesser than at the second deformation portion 74.

The embodiment according to FIG. 17 differs from the embodiment according to FIG. 15 in that three deformations portions 72 to 76 are provided, as in the embodiment according to FIG. 16. Here, the deformation portion 72 is completely surrounded by the deformation portion 74, and the deformation portion 74 is completely surrounded by the deformation portion 76. The deformability of the abutment element 72 increases from the first deformation portion 72 via the second deformation portion 74 to the third deformation portion 76.

Provision may be made that the deformability discretely increases between adjacent deformation portions. A continuous increase in the deformability may be provided.

The abutment element 22 in accordance with the embodiment in FIG. 18 has a base body 78, the shape of which largely matches the shape of the abutment element according to FIGS. 11 to 13. The sleeve-shaped portion 64 with the support members 66 is provided. However, no deformation region 58 and, in particular, no through-opening 62 is arranged on the support members 66.

Positioned in the depression 70 is a further portion 80 of the abutment element 22 against which the rod element 18 abuts. The portion 80 has a higher deformability than the base body 78 and forms a tray-shaped receptacle for the rod element 18.

In the embodiments according to FIGS. 14 and 18, provision may be made that the respective portions of the abutment element 22 are formed separate from one another and are connected to one another. Alternatively, a one-piece configuration of the respective abutment element 22 is conceivable.

What is claimed is:

1. A surgical fixation system, comprising at least one anchoring element with an anchoring portion for anchoring to a bone and with a receiving portion for a stabilization element for connecting to a further anchoring element, wherein the stabilization element is arrangeable in the receiving portion and is fixable therein by a fixing element, wherein the surgical fixation system comprises an abutment element that is arranged on the receiving portion and abuts against the anchoring portion for placement of the stabilization element, wherein the abutment element has at least one deformation region for deforming in dependence on a fixing force of the fixing element acting on the stabilization element, wherein the abutment element has a deformability, wherein the abutment element comprises a first abutment element portion having a first deformability, the first abutment element portion facing toward the stabilization element, wherein the abutment element further comprises a second abutment element portion having a second deformability, the second abutment element portion facing toward the anchoring portion, wherein the first abutment element portion comprises or forms the at least one deformation region, and wherein the first deformability is greater than the second deformability as a result of the fixing force.

2. The surgical fixation system according to claim 1, wherein the abutment element at least one of:

a) is formed separate from the receiving portion and is arranged in the receiving portion or wherein the receiving portion comprises or forms the abutment element; and
b) is of elastically or plastically deformable configuration at the at least one deformation region.

3. The surgical fixation system according to claim 1, wherein at least one deformation region is arranged at or beneath an abutment region of the abutment element for the stabilization element.

4. The surgical fixation system according to claim 1, wherein at least one deformation region is arranged at or laterally next to a lateral abutment region for the stabilization element.

5. The surgical fixation system according to claim 1, wherein the at least one deformation region at least one of:
a) has an extent in parallel to an abutment region of the abutment element for the stabilization element; and
b) is arranged or formed symmetrically on the abutment element with respect to a symmetry plane containing an axis of the receiving portion and/or the abutment element.

6. The surgical fixation system according to claim 1, wherein the at least one deformation region is formed by or comprises at least one material recess on the abutment element.

7. The surgical fixation system according to claim 6, wherein the at least one material recess:
a) is a recess on a surface of the abutment element, wherein the abutment element is deformable at a rim of the recess; or
b) is or comprises a through-opening of the abutment element.

8. The surgical fixation system according to claim 6, wherein the at least one material recess at least one of:
a) has an extent along the stabilization element arranged in the receiving portion; and
b) has an extent radially to an axis defined by the abutment element; and
c) is a cavity that is formed in the abutment element and is enclosed on all sides.

9. The surgical fixation system according to claim 1, wherein the at least one deformation region comprises a plurality of deformation regions.

10. The surgical fixation system according to claim 1, wherein the abutment element at least one of:
a) has two diametrically opposed deformation regions, the at least one deformation region comprising the two diametrically opposed deformation regions;
b) is of sleeve-shaped configuration at least in sections and has on an end face an abutment region for the stabilization element;
c) comprises two support members arranged at a distance from one another, which laterally delimit a tapering depression, wherein the stabilization element is positionable between the two support members in the tapering depression; and
d) is oriented or orientable coaxially to the receiving portion and/or to the anchoring portion.

11. The surgical fixation system according to claim 1, wherein the anchoring portion and the abutment element comprise abutment regions that are adapted to one another.

12. The surgical fixation system according to claim 1, wherein at least one of:
a) the surgical fixation system comprises at least one of the following:
two or more anchoring elements;
two or more abutment elements;
at least one stabilization element;
at least one fixing element, and
b) at least one of the following applies:
the at least one anchoring element is a bone screw;
the at least one stabilization element is a rod element;
the at least one fixing element is a screw element that is screwable to the receiving portion.

13. The surgical fixation system according to claim 1, further comprising at least one of:
a) a portion boundary, which is discrete with respect to the deformability of the abutment element, between the first abutment element portion and the second abutment element portion; and
b) a transition portion, which is present with respect to the deformability of the abutment element, by way of which the first abutment element portion and the second abutment element portion merge into one another.

14. A surgical fixation system, comprising at least one anchoring element with an anchoring portion for anchoring to a bone and with a receiving portion for a stabilization element for connecting to a further anchoring element, wherein the stabilization element is arrangeable in the receiving portion and is fixable therein by a fixing element, wherein the surgical fixation system comprises an abutment element that is arranged on the receiving portion and abuts against the anchoring portion for placement of the stabilization element, wherein the abutment element has at least one deformation region for deforming in dependence on a fixing force of the fixing element acting on the stabilization element
wherein the abutment element comprises two or more deformation portions, which comprise or are made of different materials with respect to their deformability, wherein the at least one deformation region is formed as a result of a materially different quality of the two or more deformation portions.

15. The surgical fixation system according to claim 14, wherein the abutment element has a deformability,
wherein the abutment element comprises a first abutment element portion having a first deformability, the first abutment element portion facing toward the stabilization element,
wherein the abutment element further comprises a second abutment element portion having a second deformability, the second abutment element portion facing toward the anchoring portion,
wherein the first abutment element portion comprises or forms the at least one deformation region, and
wherein the first deformability is greater than the second deformability as a result of the fixing force.

16. The surgical fixation system according to claim 15, further comprising at least one of:
a) a portion boundary, which is discrete with respect to the deformability of the abutment element, between the first abutment element portion and the second abutment element portion; and
b) a transition portion, which is present with respect to the deformability of the abutment element, by way of which the first abutment element portion and the second abutment element portion merge into one another.

17. The surgical fixation system according to claim 14, wherein the at least one deformation region is formed by or comprises at least one material recess on the abutment element.

18. The surgical fixation system according to claim 17, wherein the at least one material recess:
   a) is a recess on a surface of the abutment element, wherein the abutment element is deformable at a rim of the recess;
   or
   b) is or comprises a through-opening of the abutment element.

19. A surgical fixation system, comprising at least one anchoring element with an anchoring portion for anchoring to a bone and with a receiving portion for a stabilization element for connecting to a further anchoring element, wherein the stabilization element is arrangeable in the receiving portion and is fixable in the receiving portion by a fixing element, wherein the surgical fixation system comprises an abutment element that is arranged on the receiving portion and abuts against the anchoring portion for placement of the stabilization element, wherein the abutment element has at least one deformation region for deforming in dependence on a fixing force of the fixing element acting on the stabilization element, wherein the abutment element comprises two or more deformation portions, which comprise or are made of different materials with respect to their deformability, wherein the at least one deformation region is formed as a result of a materially different quality of the two or more deformation portions.

20. The surgical fixation system according to claim 19, wherein at least one of:
   a) the two or more deformation portions are deformation portions of the abutment element that are formed separate from one another and are joined to one another;
   and
   b) the two or more deformation portions comprise three or more deformation portions, wherein a first of the three or more deformation portions at least partially surrounds a second of the three or more deformation portions, the first of the three or more deformation portions having a first deformability, and the second of the three or more deformation portions having a second deformability, wherein the first deformability is less than the second deformability.

* * * * *